United States Patent [19]

Northeved

[11] Patent Number: 4,651,750

[45] Date of Patent: Mar. 24, 1987

[54] ELECTROMEDICAL SYSTEM

[75] Inventor: Allan Northeved, Farum, Denmark

[73] Assignee: Electronic Identification Systems Silkesborg A/S, Silkeborg, Denmark

[21] Appl. No.: 755,609

[22] Filed: Jul. 16, 1985

[30] Foreign Application Priority Data

Jul. 27, 1984 [DK] Denmark ............................ 3680/84

[51] Int. Cl.[4] ............................................... A61B 5/00

[52] U.S. Cl. .................................... 128/736; 128/903

[58] Field of Search ................................ 128/736, 903

[56] References Cited

U.S. PATENT DOCUMENTS

| | | | |
|---|---|---|---|
| 3,491,596 | 1/1970 | Dean | 128/736 |
| 3,581,570 | 6/1971 | Wortz | 128/736 |
| 3,815,583 | 6/1974 | Scheidt | 128/903 |
| 4,083,364 | 4/1978 | Kelley et al. | 128/736 |
| 4,186,749 | 2/1980 | Fryer | 128/903 |
| 4,245,652 | 1/1981 | Kelley et al. | 128/736 |
| 4,387,724 | 6/1983 | Zartman . | |

*Primary Examiner*—Kyle L Howell
*Assistant Examiner*—John C. Hanley
*Attorney, Agent, or Firm*—Ladas & Parry

[57] ABSTRACT

An electromedical system comprising a temperature sensor which can be placed in the ear of a pig. According to the invention the temperature sensor is constituted by a substantially circular resilient element fixable in the auditory meatus, and which via a conductor, e.g. a wire is connected to an outwardly located transmitter capable of transmitting the temperatures measured to one or several receivers placed at a distance therefrom. As a result a current recording of the temperature of a pig can be performed. The construction of the sensor ensures close contact with the auditory meatus, at the same time while the hearing of the animal is not affected, and normal secretion can take place.

2 Claims, 6 Drawing Figures

ELECTROMEDICAL SYSTEM

FIELD OF THE INVENTION

The invention relates to an electromedical system comprising at least one sensor, e.g. a temperature sensor which can be placed in an ear, and which via a conductor, e.g. a wire, is connected to an outwardly located transmitter capable of transmitting the temperatures measured to one or several receivers placed at a distance therefrom.

If the temperature sensor is led too deep into the auditory meatus of a pig's ear (under anaesthetics), the pig is irritated to a substantial extent. Consequently, the sensor is now placed further out, where the irritation is less.

SUMMARY OF THE INVENTION

According to the invention the temperature sensor is constituted by a substantially circular resilient element fixable in the auditory meatus.

As a result a current recording of the temperature of an animal can be performed. The construction of the sensor ensures close contact with the auditory meatus, at the same time while the hearing of the animal is not affected, and normal secretion can take place.

The substantially circular resilient element can advantageously be bent along the adjacent rims so that it is possible by means of a special set of pincers to seize these bent parts and squeeze them together during the insertion. The set of pincers may e.g. be constituted by an oblong body having resilient pincer parts in connection with a sleeve displaceable relative to the resilient pincer parts.

BRIEF DESCRIPTION OF DRAWING

The invention will be described below with reference to the accompanying drawing, in which.

DESCRIPTION OF PREFERRED EMBODIMENTS

Figure 1:
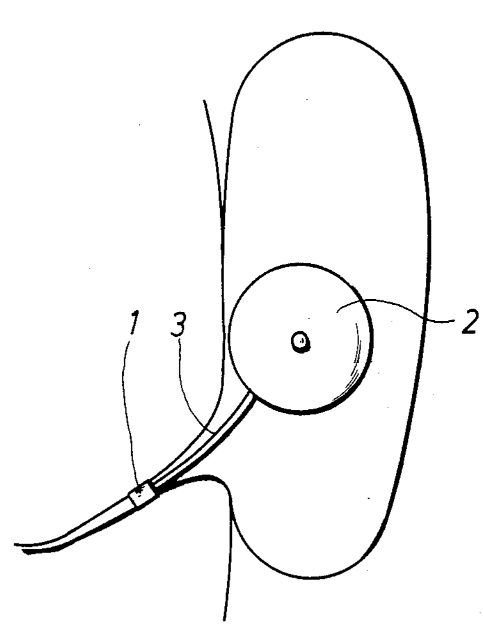
FIG. 1 illustrates a temperature sensor placed in the auditory meatus of a pig.
Figure 3:
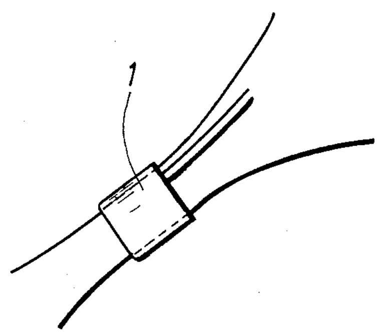
FIG. 3 is a large scale view of the temperature sensor.
Figure 4:
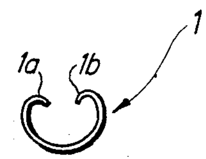
FIG. 4 is an end view of the temperature sensor.

The temperature sensor 1 shown in FIGS. 1 and 3 is adapted to be placed in the auditory meatus of a pig. If the temperature sensor 1 is led too deep into the auditory meatus, the pig is irritated to a substantial extent. Consequently, the temperature sensor 1 is now placed further out, where the irritation is less. The temperature sensor 1 is constituted by an elastic, substantially cylindrical body slotted in the longitudinal direction and bent along the almost adjacent rims—1*a,* 1*b* cf. FIG. 4—so that it is possible by means of a special set of pincers to seize these bent parts and squeeze them together during the insertion. The set of pincers is constituted by an oblong body having resilient pincer parts in connection with a sleeve displaceable relative to the resilient pincer parts.

Figure 2:
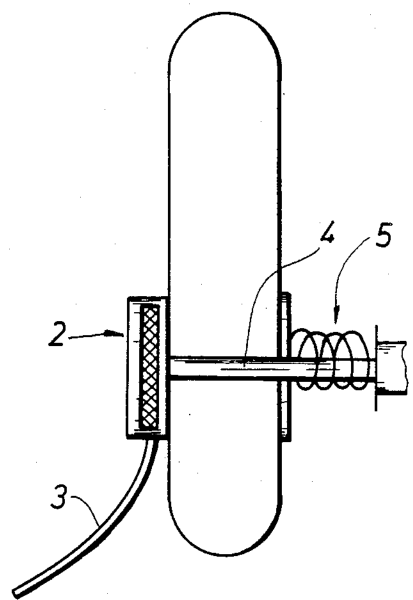
FIG. 2 illustrates a transmitter connected to the temperature sensor and fastened to the outer ear of the pig.

The sensor, which may e.g. comprise a temperature sensitive resistor is connected to an outwardly located transmitter—cf. FIGS. 1 and 2—fastened to the outer ear by means of a pin 4 led through the ear. The transmitter 2 can by wireless signal transfer transmit the temperatures measured to one or several receivers located at a distance therefrom. Consequently, a current recording of the temperature of an animal can be performed. The sensor is made of a resilient material and is of a cross section corresponding to part of a circular arc. The sensor is thus in close contact with the auditory meatus, at the same time while the hearing of the animal is not affected, and normal secretion can take place.

Figure 5:
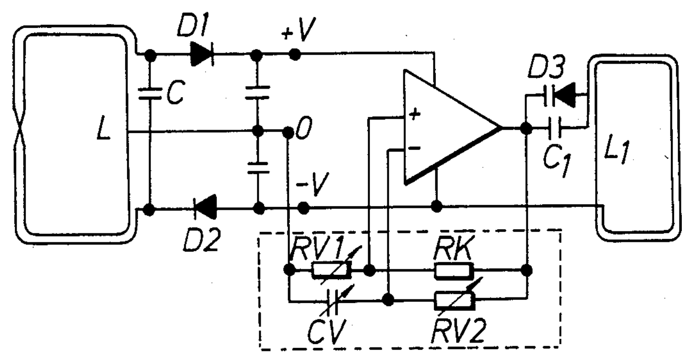
FIG. 5 is an example of how the transmitter may be constructed.

An example of a sensor with associated transmitter is shown in FIG. 5. It comprises an antenna L for receiving energy, a low frequency oscillator having parametersensitive elements and an antenna $L_1$ for transmitting parameter-dependent signals. The frequency of the low frequency oscillator is solely determined by the four components $RV_1$, RK, CV an $RV_2$ of the sensor, the resistor RK, however, being constant and being used for calibrating the sensor. Both the capacitor CV and the resistors $RV_1$ and $RV_2$ are variable and have a negative temperature co-efficient and will at rising temperatures cause a rise in frequency. Using generally accessible components, the sensor circuit shown will give a change of frequency of approx 5% per °C. The oscillator transmits a square wave signal capable of bringing an LC-circuit for the transmitter signal in oscillation with a pulsating high frequency. A capacity diode $D_3$ causes a change of frequency for every second impulse, thus ensuring reception despite strong interference from outside sources.

Only one of the sensor components needs to be variable. This may be used for other measurings. If, for example $RV_1$ is a field-effect transistor and the other components are constant, the circuit will be able to transmit EKG-signals. Similarly, a capacity pressure transducer in CV's place would be able to measure pulsation or blood pressure. Several of the circuits mentioned may be present in one and the same unit and connected to the same transmitter antenna. The signal thus produced will be a pulsating complex FM-signal, in which the individual parameters may be easily derived in low frequency filters after detection.

It should be mentioned that the supply of voltage to the low frequency oscillator is balanced, whereby the frequency becomes independent of the voltage supply.

The temperature-sensitive elements may alternatively comprise a series of temperature-sensitive semi-conductor elements in the form of a custom-design-integrated circuit inserted in the substantially cylindrical body.

The cylindrical body itself is either made of metal of of plastics, the rims preferably being rounded.

According to the invention an electromedical system is thus provided making it possible for a pig-breeder to supervise the entire herd of pigs and interfere as quickly as possible in case diseases should break out.

Figure 6:
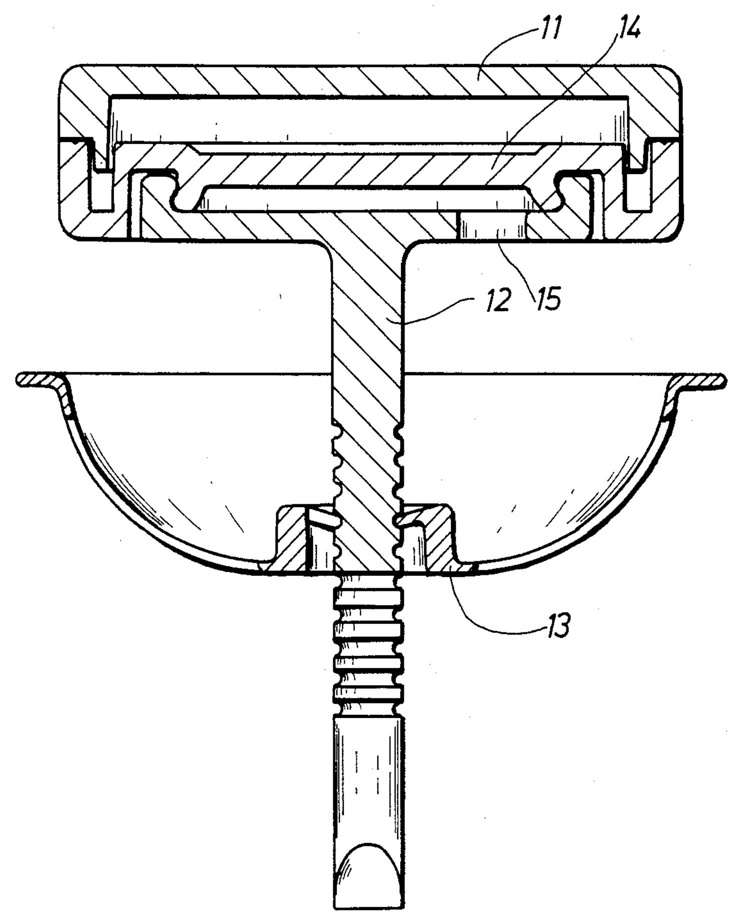
FIG. 6 is a fastening means for the sensor.

FIG. 6 is an example of a fastening means for the sensor. The part 11 is the actual transponder capsule which is closed by means of an ultrasonic welding. The part 12 and the part 13 constitute the very fastening means. The part 12 is at the bottom provided with a cut so that it can be stuck through the ear of a pig or a cow, whereafter the part 13 is pushed up around the pin and locked. The part 13 is slotted in such a manner that it may be resilient, e.g. when the pig or the cow grows, and the ear grows thicker. In the opposite end the part 12 is constructed in such a manner that it may be buttoned onto the transponder. If a pull is excerted in the transponder and the part 12 in an attempt to separate the parts, the tension of the part 12 around the part 14 will be even firmer and thus nearly make a separation impossible.

The parts are separable by means of a small aperture 15 in the right side of the part 12, as a small tilting implement is inserted through this aperture, so that the parts can be tilted away from each other. The tilting implement is for example used in case the transponder is to be replaced. If the fastening means is to be removed, the part 13 is rolled backwards and the pin tilted so that the parts are separable.

The electromedical system according to the invention may be varied in many ways without thereby deviating from the scope of the invention.

I claim:

1. In an electromedical system including at least one physiological sensor, e.g. a temperature sensor, which can be placed in an ear and which via a conductor, e.g. a wire connected to a transmitter adapted to be fixed to the outer ear, is capable of transmitting the temperature measured to one or several receivers placed at a distance therefrom, the improvement wherein said temperature sensor comprises a hollow substantially cylindrical resilient band-like element including a longitudinal slot extending along a peripheral surface, said sensor being adapted to be fixed in the auditory meatus.

2. An electromedical system according to claim 6 wherein the band-like element includes rims along the slot curved toward the axis of the cylinder.

* * * * *